(12) United States Patent
Lee et al.

(10) Patent No.: US 9,853,226 B2
(45) Date of Patent: Dec. 26, 2017

(54) FUSED POLYCYCLIC HETEROAROMATIC COMPOUND, ORGANIC THIN FILM INCLUDING COMPOUND AND ELECTRONIC DEVICE INCLUDING ORGANIC THIN FILM

(71) Applicant: Samsung Electronics Co., Ltd., Suwon-si, Gyeonggi-do (KR)

(72) Inventors: Don-Wook Lee, Seoul (KR); Jeong Il Park, Seongnam-si (KR); Eun Kyung Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/188,365

(22) Filed: Jun. 21, 2016

(65) Prior Publication Data
US 2017/0069854 A1    Mar. 9, 2017

(30) Foreign Application Priority Data

Sep. 8, 2015  (KR) .................. 10-2015-0127165

(51) Int. Cl.
*H01L 51/00* (2006.01)
*C07D 495/22* (2006.01)
*H01L 51/05* (2006.01)

(52) U.S. Cl.
CPC ........ *H01L 51/0074* (2013.01); *C07D 495/22* (2013.01); *H01L 51/0541* (2013.01); *H01L 51/0545* (2013.01); *H01L 51/0558* (2013.01)

(58) Field of Classification Search
CPC .................................................. H01L 51/0074
USPC ......................................................... 549/41
See application file for complete search history.

(56) References Cited

U.S. PATENT DOCUMENTS

| | | | |
|---|---|---|---|
| 6,913,710 | B2 | 7/2005 | Farrand et al. |
| 7,816,673 | B2 | 10/2010 | Park et al. |
| 8,658,805 | B2 | 2/2014 | Park et al. |
| 2010/0032658 | A1 | 2/2010 | Lee et al. |
| 2010/0065826 | A1 | 3/2010 | Takimiya et al. |
| 2013/0320316 | A1 | 12/2013 | Park et al. |
| 2015/0166560 | A1 | 6/2015 | Kitamura et al. |

FOREIGN PATENT DOCUMENTS

| | | |
|---|---|---|
| JP | 2009-267132 A | 11/2009 |
| JP | 2010-095644 A | 4/2010 |
| JP | 2013-201363 A | 10/2013 |
| JP | 2014-045099 A | 3/2014 |
| JP | 2015-017052 A | 1/2015 |
| KR | 2010-0007780 A | 1/2010 |
| KR | 2013-0136938 A1 | 12/2013 |
| WO | WO-2008-050726 A1 | 5/2008 |
| WO | WO-2009/009790 A1 | 1/2009 |
| WO | WO-2012-135133 A1 | 10/2012 |
| WO | WO-2013-124688 A2 | 8/2013 |

OTHER PUBLICATIONS

Liquid Crystals (2000), 27(3), 321-328.
Journal of Materials Science (2015), 50(5), 2263-2271.
Organic Letters (2004), 6(19), 3413-3416.
Angewandte Chemie, International Edition (2011), 50(28), 6320-6323.

*Primary Examiner* — Taofiq A Solola
(74) *Attorney, Agent, or Firm* — Harness, Dickey & Pierce, P.L.C.

(57) ABSTRACT

A low-molecular-weight fused polycyclic heteroaromatic compound includes a compound represented by Chemical Formula 1A, a compound represented by Chemical Formula 1B, or a combination thereof. The fused polycyclic heteroaromatic compound has a compact planar structure in which five or more aromatic rings are fused together, and thereby exhibit higher charge mobility, and furthermore, enables the use of a deposition process or a room-temperature (about 20 to about 25° C.) solution process when applied to devices, therefore realizing improved processibility.

11 Claims, 1 Drawing Sheet

FUSED POLYCYCLIC HETEROAROMATIC COMPOUND, ORGANIC THIN FILM INCLUDING COMPOUND AND ELECTRONIC DEVICE INCLUDING ORGANIC THIN FILM

CROSS REFERENCE TO RELATED APPLICATION

This application claims priority to and the benefit of Korean Patent Application No. 10-2015-0127165 filed in the Korean Intellectual Property Office on Sep. 8, 2015, the entire contents of which are incorporated herein by reference.

BACKGROUND

1. Field

Example embodiments relate to a fused polycyclic heteroaromatic compound, an organic thin film, and an electronic device including the organic thin film.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, research on a polymer organic material, for example, polythiophene, or a low molecular organic material, for example, pentacene, as an organic semiconductor material used for a channel of a thin film transistor have been made.

However, the polymer organic material has relatively low charge mobility but a relatively high blocking leakage current. On the other hand, the low molecular organic material (e.g., pentacene, etc.) is reported to have relatively high charge mobility of greater than or equal to about 3.2 to about 5.0 cm²/Vs, but needs expensive vacuum deposition equipment to form a thin film, and thus may not be appropriate in terms of processibility and formation of a large area.

Accordingly, development of a new organic semiconductor material simultaneously having improved electrical characteristics and improved processibility is continuously required.

SUMMARY

Example embodiments provide a low-molecular-weight fused polycyclic heteroaromatic compound that has a compact planar structure in which five or more aromatic rings are fused together, and thereby exhibits relatively high charge mobility, and furthermore, enables the use of a deposition process or a room-temperature (about 20 to about 25° C.) solution process when applied to devices, therefore realizing improved processibility.

Example embodiments also provide an organic thin film including the fused polycyclic heteroaromatic compound.

Example embodiments also provide an electronic device including the organic thin film as a carrier transport layer.

According to example embodiments, a fused polycyclic heteroaromatic compound is selected from a compound represented by Chemical Formula 1A, a compound represented by Chemical Formula 1B, and a combination thereof.

[Chemical Formula 1A]

[Chemical Formula 1B]

In Chemical Formulae 1A and 1B, each of $Ar^1$, $Ar^2$, and $Ar^3$ are independently selected from phenylene, naphthalene, and anthracene, a, b, and c correspond to the number of hydrogens bound to carbon of $Ar^1$, $Ar^2$, and $Ar^3$, each of $X^1$ and $X^2$ are independently selected from S, Se, Te, and N—$R^a$, wherein $R^a$ is independently selected from hydrogen and a linear or branched $C_1$ to $C_{10}$ alkyl group, each of $X^3$ and $X^4$ are independently selected from O, S, Se, Te, N—$R^a$, and $C(R^b)$=$C(R^c)$, wherein $R^a$, $R^b$, and $R^c$ are independently selected from hydrogen and a linear or branched $C_1$ to $C_{10}$ alkyl group, each of $R^1$ to $R^7$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, one of $R^1$ and $R^2$, and $R^3$ and $R^4$, are linked with each other to provide one of a $C_5$ aromatic ring and a $C_6$ aromatic ring, n1 is 0 or 1, n2 is 0 or 1, and n1+n2 are greater than or equal to 1, and at least one hydrogen of the aromatic ring at an outermost position of Chemical Formulae 1A and 1B is substituted with a functional group represented by Chemical Formula 2.

[Chemical Formula 2]

$$*-L \!-\!\!\left[Y^1\!-\!(CR^pR^q)\!-\!\!-\!(CR^rR^s)_p\right]_{\!q}\!\!Y^2\!-\!(CR^xR^y)_r\!-\!R^z$$

In Chemical Formula 2,

L is selected from a single bond, a substituted or unsubstituted $C_1$ to $C_{20}$ alkylene group, a substituted or unsubstituted $C_6$ to $C_{30}$ arylene group, and a substituted or unsubstituted $C_3$ to $C_{30}$ heteroarylene group, each of $Y^1$ and $Y^2$ are independently selected from O, S, Se, Te, and NH, each of $R^p$ and $R^q$ are independently selected from hydrogen and a $C_1$ to $C_6$ alkyl group, each of $R^r$, $R^s$, $R^x$, $R^y$, and $R^z$ are independently selected from hydrogen, $C_1$ to $C_6$ alkyl group, a $C_6$ to $C_{10}$ aryl group, and a $C_3$ to $C_{10}$ heteroaryl group, p is an integer ranging from 1 to 5, q is an integer ranging from 1 to 30, and r is an integer ranging from 0 to 2.

In Chemical Formulae 1A and 1B, each of $X^1$, $X^2$, $X^3$, and $X^4$ may independently be selected from one of a sulfur atom (S) and a selenium atom (Se).

In Chemical Formulae 1A and 1B, $X^1$ and $X^2$ are sulfur atoms (S), and $X^3$ and $X^4$ are selenium atoms (Se).

one of the $C_5$ aromatic ring and $C_6$ aromatic ring may independently be an $X^5$-containing ring and an $X^6$-containing ring, the $X^5$ and $X^6$ may be independently selected from O, S, Se, Te, N—$R^a$, and C($R^b$)=C($R^c$), wherein $R^a$, $R^b$ and $R^c$ may be independently selected from hydrogen and a linear or branched $C_1$ to $C_{10}$ alkyl group.

At least one of $R^1$ and $R^4$ of one of Chemical Formula 1A and 1B may be a polar functional group of Chemical Formula 2, and the fused polycyclic heteroaromatic compound of one of Chemical Formula 1A and 1B is linear.

In example embodiments, the L of Chemical Formula 2 may be represented by Chemical Formula 3.

[Chemical Formula 3]

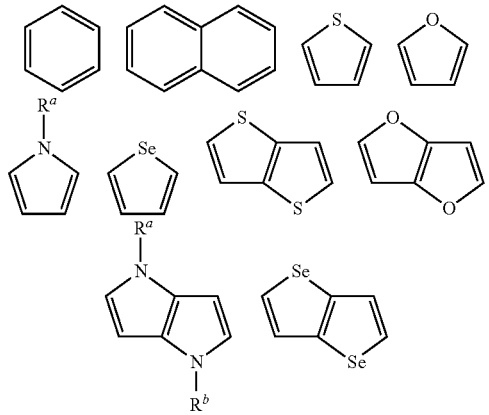

In Chemical Formula 3, each of $R^a$ and $R^b$ may be independently selected from hydrogen and a linear or branched $C_1$ to $C_{10}$ alkyl group.

The fused polycyclic heteroaromatic compound may have an average molecular weight of about 300 to about 3,000.

Specific examples of the fused polycyclic heteroaromatic compound may be compounds (1) to (24).

(1)

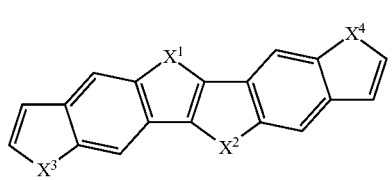

(2)

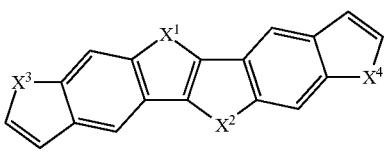

(3)

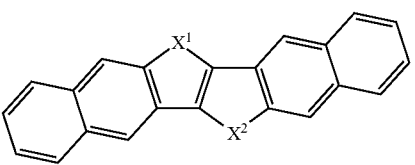

(4)

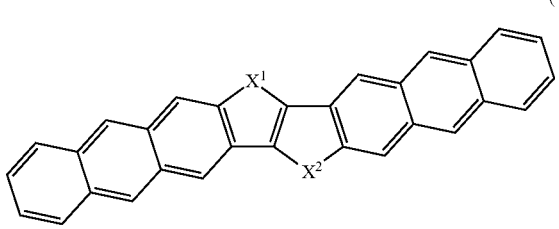

(5)

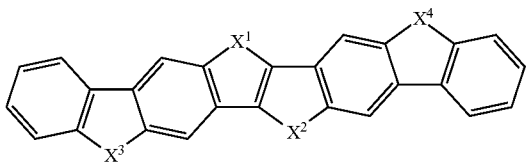

(6)

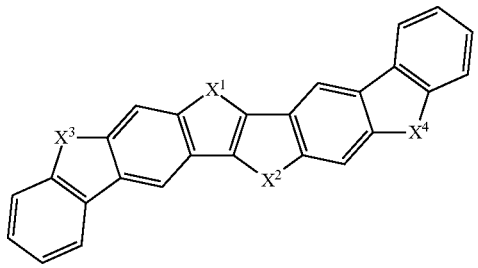

(7)

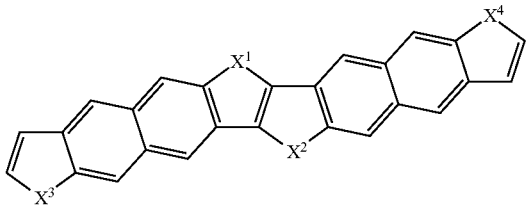

(8)

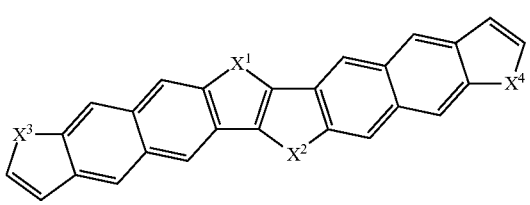

(9)
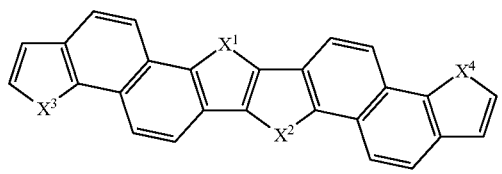
(10)
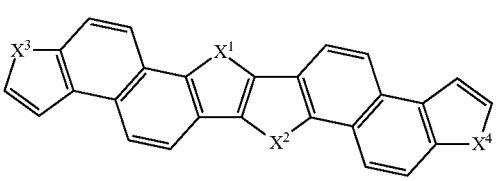
(11)
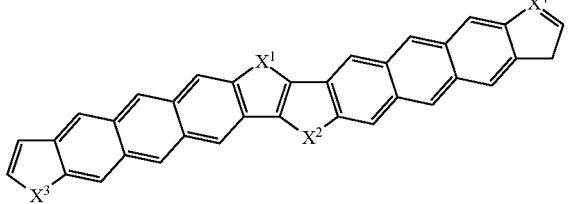
(12)
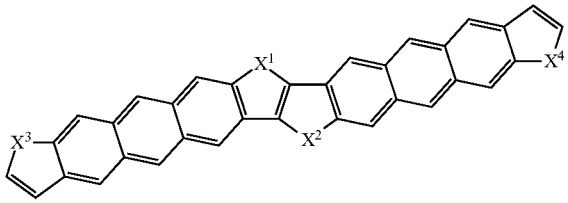
(13)
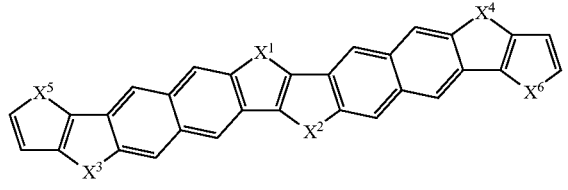
(14)
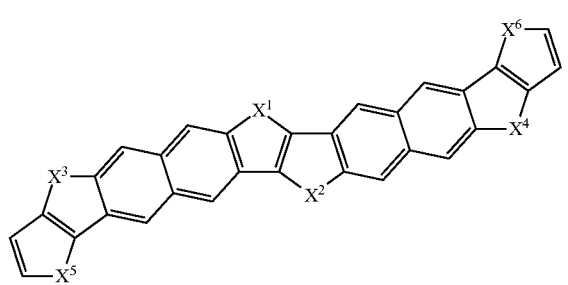
(15)
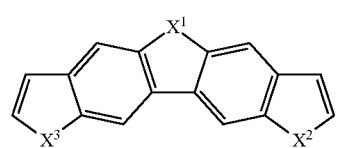
(16)
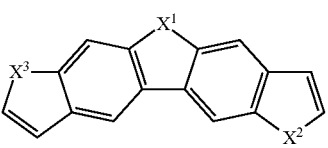
(17)
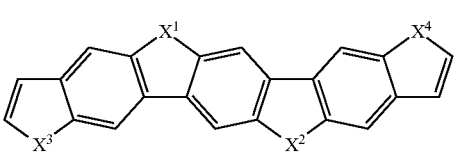
(18)
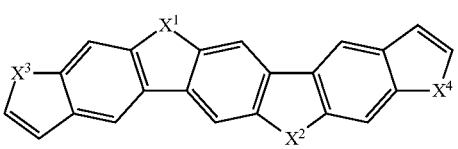
(19)
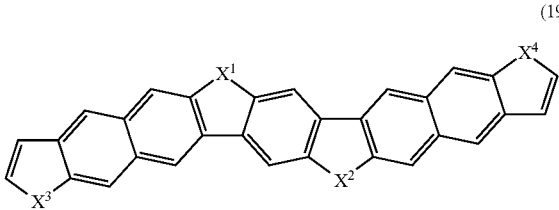
(20)
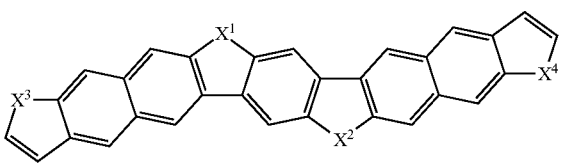
(21)
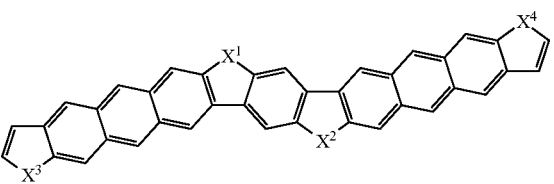
(22)
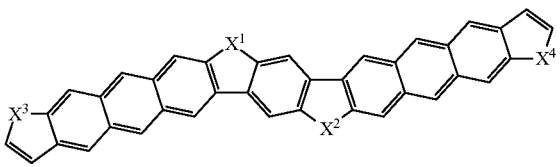
(23)
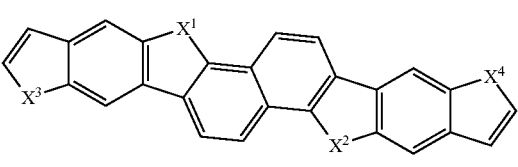

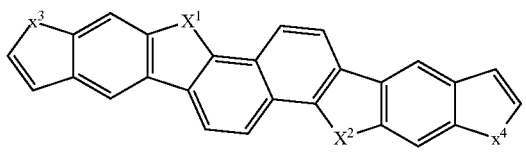

(24)

In the compounds (1) to (24), each of $X^1$, $X^2$, $X^3$, and $X^4$ are the same in Chemical Formulae 1A and 1B, and the $X^5$ and $X^6$ are independently selected from O, S, Se, Te, N—$R^a$, and $C(R^b)$=$C(R^c)$, wherein $R^a$, $R^b$, and $R^c$ are independently selected from hydrogen and a linear or branched $C_1$ to $C_{10}$ alkyl group.

In the compounds (1) to (24), a hydrogen of each aromatic ring may be replaced by a $C_1$ to $C_{10}$ linear or branched alkyl group, and at least one hydrogen in an outermost aromatic ring may be replaced by the substituent represented by Chemical Formula 2.

According to example embodiments, an organic thin film and an electronic device includes the fused polycyclic heteroaromatic compound.

DETAILED DESCRIPTION

Figure 1:
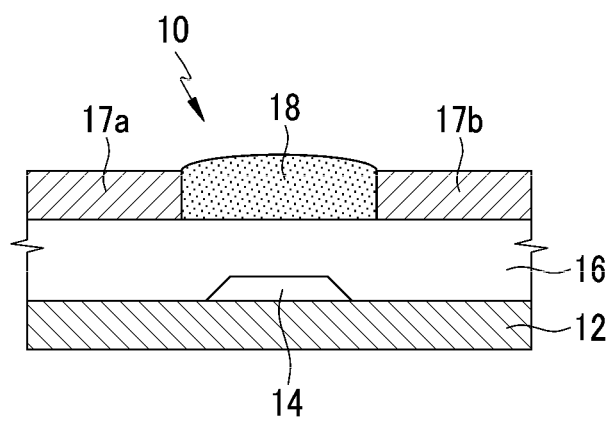
FIG. 1 is a schematic cross-sectional view showing a transistor according to example embodiments.

This disclosure will be described more fully hereinafter in the following detailed description of this disclosure, in which some but not all embodiments of this disclosure are described. However, this disclosure may be embodied in many different forms and is not construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, the term "combination thereof" refers to a substituent, a mixture, or a stacked structure.

As used herein, when a definition is not otherwise provided, the term "hetero" may refer to one including 1 to 4 heteroatoms selected from N, O, S, Se, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. The term "heterocycloalkyl group" may be at least one non-aromatic ring including a heteroatom, and the term "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

The term "aryl group" may refer to a monovalent functional group formed by the removal of one hydrogen atom from one or more rings of an arene, e.g., phenyl or naphthyl. The arene may refer to a hydrocarbon having an aromatic ring, and includes monocyclic and polycyclic hydrocarbons wherein the additional ring(s) of the polycyclic hydrocarbon may be aromatic or nonaromatic.

The "arylalkyl group" may refer to aryl group where at least one hydrogen is substituted with a lower alkylene, e.g., methylene, ethylene, propylene, etc. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "heteroarylalkyl group" may refer to the alkyl group defined above where at least one hydrogen is substituted with a heteroaryl group.

The term "alkylheteroaryl group" may refer to the heteroaryl group defined above where at least one hydrogen is substituted with alkyl group.

As used herein, when a definition is not otherwise provided, the term "aromatic ring" refers to a functional group in which all atoms in the cyclic functional group have a p-orbital, wherein these p-orbitals are conjugated. For example, the aromatic ring may be a $C_6$ to $C_{20}$ aryl group.

As used herein, when a definition is not otherwise provided, the term "substituted" means that a compound or group is substituted with at least one substituent selected independently from a halogen (—F, —Cl, —Br, or —I), a $C_1$ to $C_{30}$ linear or branched alkyl group, for example, a $C_1$ to $C_{10}$ linear or branched alkyl group, a $C_2$ to $C_{30}$ linear or branched alkenyl group, for example, a $C_2$ to $C_{10}$ linear or branched alkenyl group, a $C_2$ to $C_{30}$ linear or branched alkynyl group, for example a $C_2$ to $C_{10}$ linear or branched alkynyl group, a $C_6$ to $C_{30}$ aryl group, for example a $C_6$ to $C_{12}$ aryl group, a $C_2$ to $C_{30}$ heteroaryl group, for example a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+1}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein R and R' are independently hydrogen or a $C_1$ to $C_{10}$ alkyl group), an amidino group (—C(=NH)NH$_2$), a nitro group (—NO$_2$), an amide group (—C(=O)N(H)R, wherein R is hydrogen or a $C_1$ to $C_{10}$ alkyl group), an aldehyde group (—C=O)H), a hydroxyl group (—OH), a sulfonyl group (—S (=O)$_2$R, wherein R is independently hydrogen or a $C_1$ to $C_{10}$ alkyl group), and a carbamate group (—NH$_2$C(=O)OR, wherein R is a $C_1$ to $C_{10}$ alkyl group) instead of hydrogen, provided that the substituted atom's normal valence is not exceeded.

According to example embodiments, a fused polycyclic heteroaromatic compound having a compact planar structure in which five or more rings may be fused together and is represented by one of Chemical Formula 1A and 1B is provided.

[Chemical Formula 1A]

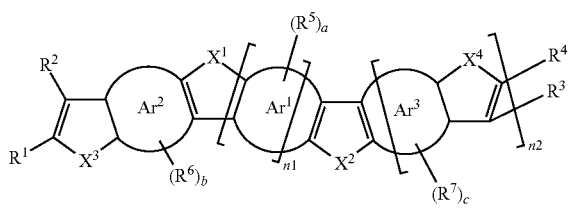

[Chemical Formula 1B]

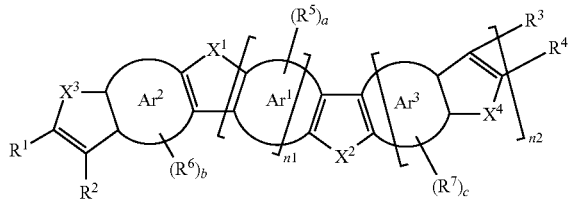

In Chemical Formulae 1A and 1B, $Ar^1$, $Ar^2$, and $Ar^3$ are independently selected from phenylene, naphthalene, and anthracene, a, b and c correspond to the number of hydrogen bound to carbon of the $Ar^1$, $Ar^2$, and $Ar^3$, $X^1$ and $X^2$ are independently selected from S, Se, Te, and N—$R^a$, wherein $R^a$ are independently selected from hydrogen and a linear or branched $C_1$ to $C_{10}$ alkyl group, $X^3$ and $X^4$ are independently selected from O, S, Se, Te, N—$R^a$, and C($R^b$)=C($R^c$), wherein $R^a$, $R^b$, and $R^c$ are independently selected from hydrogen and linear or branched $C_1$ to $C_{10}$ alkyl group, $R^1$ to $R^7$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, or $R^1$ and $R^2$ are linked with each other to provide a $C_5$ aromatic ring or a $C_6$ aromatic ring, or $R^3$ and $R^4$ are linked with each other to provide a $C_5$ aromatic ring or a $C_6$ aromatic ring, at least one hydrogen of the aromatic ring at an outermost position of Chemical Formulae 1A and 1B is substituted with a functional group represented by Chemical Formula 2, n1 is 0 or 1, n2 is 0 or 1, and n1+n2 are greater than or equal to 1.

In Chemical Formulae 1A and 1B, when n2 is 0, $R^3$ and $R^4$ may be present as a substituent of an $X^2$-containing ring.

[Chemical Formula 2]

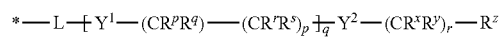

In Chemical Formula 2,

L is selected from a single bond, a substituted or unsubstituted $C_1$ to $C_{20}$ alkylene group, for example a substituted or unsubstituted $C_1$ to $C_{12}$ alkylene group, a substituted or unsubstituted $C_6$ to $C_{30}$ arylene group, a substituted or unsubstituted $C_6$ to $C_{18}$ arylene group, and a substituted or unsubstituted $C_3$ to $C_{30}$ heteroarylene group, for example a substituted or unsubstituted $C_3$ to $C_{12}$ heteroarylene group, $Y^1$ and $Y^2$ are independently selected from O, S, Se, Te, and NH, $R^p$ and $R^q$ are independently selected from hydrogen and a $C_1$ to $C_6$ alkyl group, $R^r$, $R^s$, $R^x$, $R^y$, and $R^z$ are independently selected from hydrogen and a $C_1$ to $C_6$ alkyl group, p is an integer ranging from 1 to 5, q is an integer ranging from 1 to 30, for example, 1 to 20 or 1 to 10, and r is an integer ranging from 0 to 2.

In Chemical Formula 2, * indicates a position where the Chemical Formula 2 is bound to Chemical Formula 1A or 1B.

The fused polycyclic heteroaromatic compound represented by Chemical Formula 1A or 1B has a structure that five or more, for example seven or more or eight or more aromatic rings and heteroaromatic rings are fused. By having a compact planar molecular structure, the fused polycyclic heteroaromatic compound has a uniform and stable oxidation potential, when applied to an actual device and shows relatively high charge mobility because the intermolecular packing and stacking are improved. Thereby, the compound may be more easily synthesized and effectively applied to a semiconductor material, an electron transporting material, etc. In addition, the fused polycyclic heteroaromatic compound includes a hydrophilic polar functional group represented by Chemical Formula 2 at the terminal end to improve organic dissolubility for a solvent. This dissolubility improvement may not only make the compound simply coated through a room temperature solution process but also form a thin film having a large area, and accordingly, the compound is effective in terms of processibility and workability. In addition, when the compound is formed in a form of a thin film through a deposition process, a given or predetermined intermolecular arrangement may be included, improving uniformity of the thin film.

In Chemical Formulae 1A and 1B, $X^1$, $X^2$, $X^3$, and $X^4$ may independently be selected from a sulfur atom (S) or a selenium atom (Se). In Chemical Formulae 1A and 1B, $X^1$ and $X^2$ may be sulfur atoms (S) and $X^3$ and $X^4$ may be selenium atoms (Se). In Chemical Formulae 1A and 1B, $X^1$ and $X^2$ is S or Se, intermolecular packing or stacking is improved.

In Chemical Formulae 1A and 1B, $X^1$ and $X^2$, and $X^3$ and $X^4$ are respectively symmetrically present each other, and thus intermolecular packing or stacking characteristics may be further improved.

In Chemical Formulae 1A and 1B, when n1 is 1, at least one fused phenylene, naphthalene, or anthracene ring may be positioned among heterorings of an $X^1$-containing ring and an $X^2$-containing ring to expand a conjugation structure and thus, increase an interaction among molecules and resultantly, improve charge mobility and thermal stability.

In Chemical Formulae 1A and 1B, when $Ar^1$, $Ar^2$, and $Ar^3$ are phenylene, a, b, and c are independently an integer ranging from 0 to 2, when $Ar^1$, $Ar^2$, and $Ar^3$ is naphthalene, a, b, and c are independently an integer ranging from 0 to 4, and when $Ar^1$, $Ar^2$, and $Ar^3$ is anthracene, a, b, and c are independently an integer ranging from 0 to 6. When a, b, and c are greater than or equal to about 2, a plurality of $R^5$, $R^6$, and $R^7$ may be the same or different.

In example embodiments, $R^5$, $R^6$, and $R^7$ of the fused polycyclic heteroaromatic compound represented by Chemical Formulas 1A or 1B may be hydrogen. Herein, linearity of the fused polycyclic heteroaromatic compound is improved, and an advantageous packing structure for a charge transfer may be provided.

When the $R^1$ and $R^2$ are fused each other and form a $C_5$ aromatic ring or a $C_6$ aromatic ring, or when $R^3$ and $R^4$ are fused each other and form a $C_5$ aromatic ring or a $C_6$ aromatic ring, the aromatic rings may be respectively an $X^5$-containing ring and an $X^6$-containing ring, the $X^5$ and $X^6$ are independently selected from O, S, Se, Te, N—$R^a$, and $C(R^b)=C(R^c)$, and herein, $R^a$, $R^b$, and $R^c$ are independently hydrogen or a linear or branched $C_1$ to $C_{10}$ alkyl group. Specific examples of the $C_5$ and $C_6$ aromatic rings may be a thiophene ring, a selenophene ring, a furan ring, a benzene ring, etc.

Because a polar functional group of Chemical Formula 2 is induced at the terminal end of the aromatic ring of the fused polycyclic heteroaromatic compound represented by Chemical Formula 1A or 1B, organic dissolubility for a solvent may be improved. In addition, when the compound is used to form a thin film through a deposition process, a given or predetermined intermolecular arrangement may be induced, improving charge mobility.

The polar functional group of Chemical Formula 2 is positioned at the terminal end of the aromatic ring of the fused polycyclic heteroaromatic compound represented by Chemical Formula 1A or 1B and herein, may maintain linearity of the fused polycyclic heteroaromatic compound. In other words, the polar functional group of Chemical Formula 2 may be substituted at a position of $R^1$ and/or $R^4$ of the fused polycyclic heteroaromatic compound represented by Chemical Formula 1A or 1B. Herein, the intermolecular arrangement of the compound in a thin film state may be adjusted to be uniform.

In example embodiments, L of Chemical Formula 2 may be selected from a substituted or unsubstituted $C_1$ to $C_{20}$ alkylene group, for example a substituted or unsubstituted $C_1$ to $C_{12}$ alkylene group, a substituted or unsubstituted $C_6$ to $C_{30}$ arylene group, a substituted or unsubstituted $C_6$ to $C_{18}$ arylene group and a substituted or unsubstituted $C_3$ to $C_{30}$ heteroarylene group, for example a substituted or unsubstituted $C_3$ to $C_{12}$ heteroarylene group.

In example embodiments, L of Chemical Formula 2 may be represented by Chemical Formula 3.

[Chemical Formula 3]

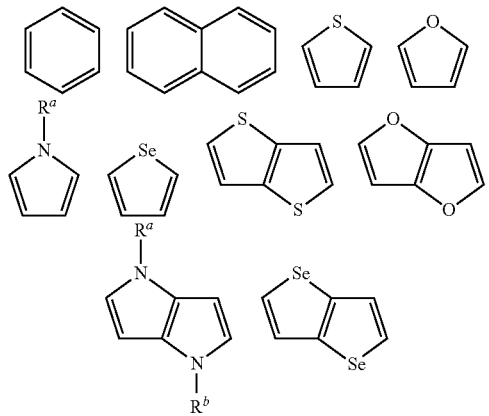

In Chemical Formula 3, $R^a$ and $R^b$ are independently selected from hydrogen and a linear or branched $C_1$ to $C_{10}$ alkyl group.

In Chemical Formula 3, one of two carbons of the aromatic ring is bound to Chemical Formula 1A or Chemical Formula 1B, and the other is bound to $Y^1$ of Chemical Formula 2. Bonding positions are not particularly limited. The remaining hydrogen except the two bonding groups may be replaced by a $C_1$ to $C_{30}$ linear or branched alkyl group.

Examples of the polar functional group of Chemical Formula 2 may be a functional group represented by one of Chemical Formulae 2-1 to 2-3.

[Chemical Formula 2-1]

\*—CH$_2$—(O—CH$_2$—CH$_2$)$_q$—O—CH$_2$—CH$_3$

[Chemical Formula 2-2]

\*—CH$_2$—(S—CH$_2$—CH$_2$)$_q$—S—CH$_2$—CH$_3$

[Chemical Formula 2-3]

\*—CH$_2$—(Se—CH$_2$—CH$_2$)$_q$—Se—CH$_2$—CH$_3$

In Chemical Formulae 2-1 to 2-3, q is an integer ranging from 1 to 30.

In Chemical Formulae 2-1 to 2-3, \* indicates a position where the Chemical Formula 2 is bound to Chemical Formula 1A or 1B.

The fused polycyclic heteroaromatic compound according to example embodiments may have an average molecular weight of about 300 to about 3000, for example about 300 to about 1000. When the fused polycyclic heteroaromatic compound has the average molecular weight within the range, the fused polycyclic heteroaromatic compound may be more easily handled.

Specific examples of the fused polycyclic heteroaromatic compound may be compound (1) to (24).

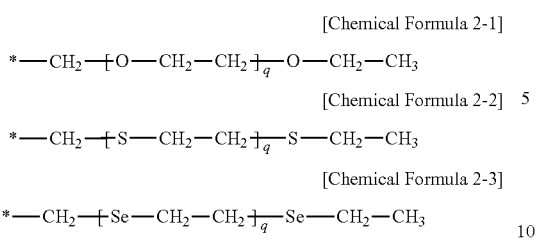
(1)

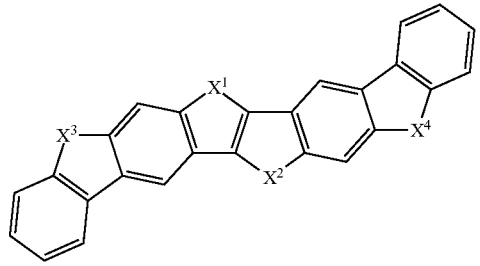
(2)

(3)

(4)

(5)

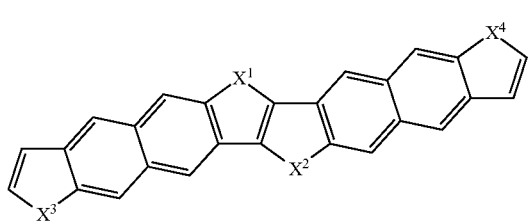
(6)

(7)

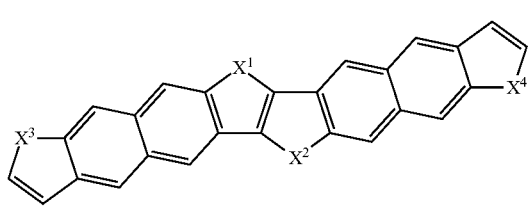
(8)

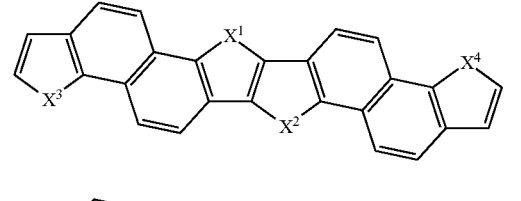
(9)

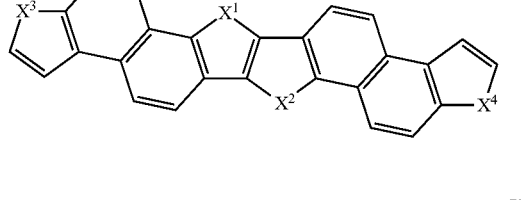
(10)

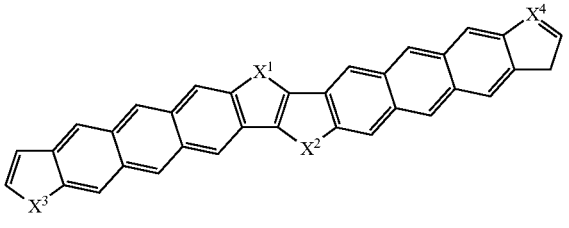
(11)

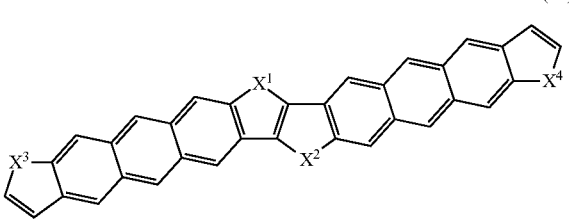
(12)

-continued

(13)
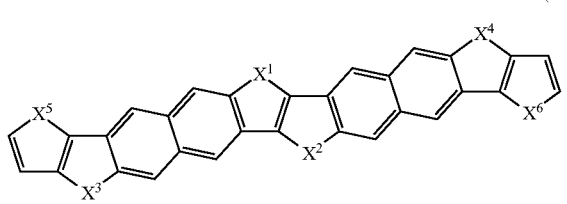

(14)
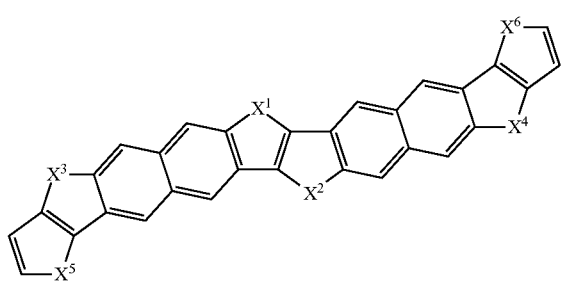

(15)
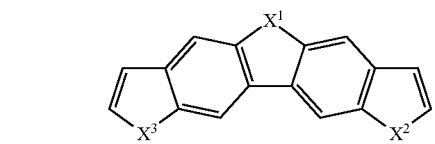

(16)
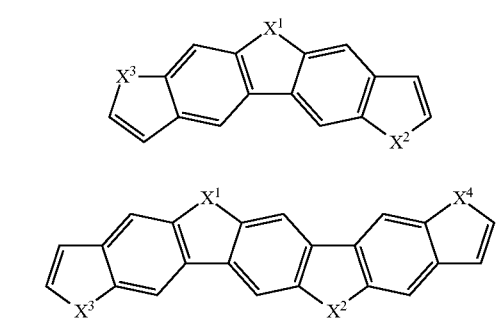

(17)
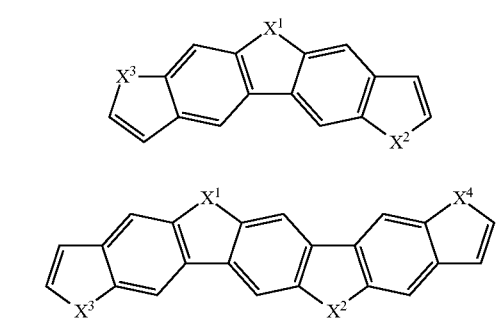

(18)
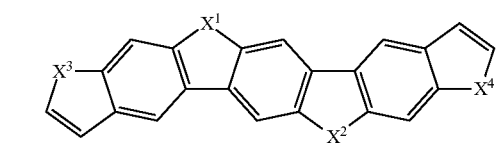

(19)
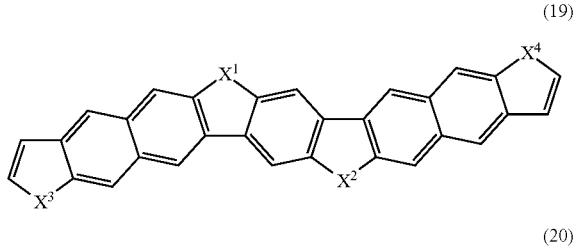

(20)
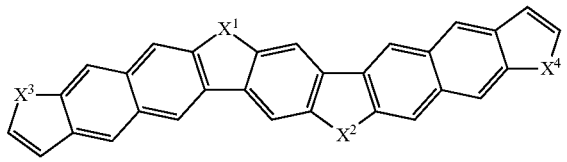

-continued

(21)
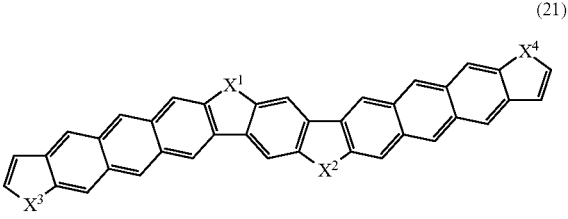

(22)
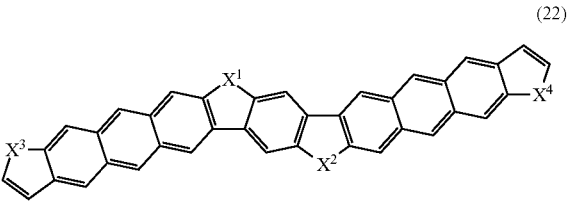

(23)
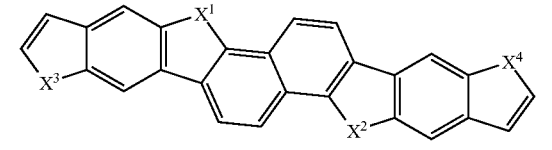

(24)
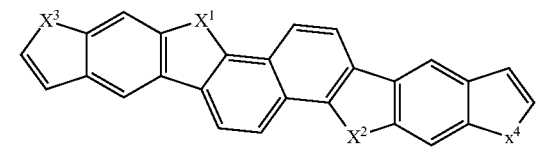

In the compounds (1) to (24), $X^1$, $X^2$, $X^3$, and $X^4$ are the same in Chemical Formulae 1A and 1B, and the $X^5$ and $X^6$ are independently selected from O, S, Se, Te, N—$R^a$, and $C(R^b)$=$C(R^c)$, wherein $R^a$, $R^b$, and $R^c$ are independently selected from hydrogen and a linear or branched $C_1$ to $C_{10}$ alkyl group.

In the compounds (1) to (24), each aromatic ring may be replaced by a substituent, for example a $C_1$ to $C_{10}$ linear or branched alkyl group.

In the compounds (1) to (24), at least one hydrogen in an outermost aromatic ring may be replaced by the substituent represented by Chemical Formula 2.

Herein, the polar functional group of Chemical Formula 2 is positioned at the terminal end of the aromatic ring of the fused polycyclic heteroaromatic compound of each compound 1 to 24 and may maintain linearity of the fused polycyclic heteroaromatic compound. For example, as for a 5-membered aromatic ring containing a hetero atom, the polar functional group may be present at a position of No, 1, and as for a 6-membered aromatic ring, the polar functional group may be positioned at a position of No. 2 or 3. Herein, the intermolecular arrangement of the compound in a thin film state may be adjusted to be uniform.

The fused polycyclic heteroaromatic compound according to example embodiments may be prepared according to a general method, for example, chemical or electrochemical oxidation synthesis, which is a representative method of polymerizing an aromatic compound or a heteroaromatic compound, or condensation polymerization using a compound of an organic transition element, e.g., nickel or palladium.

According to example embodiments, an organic thin film including the fused polycyclic heteroaromatic compound and an electronic device including the organic thin film are provided.

The organic thin film according to example embodiments includes the fused polycyclic heteroaromatic compound, so the organic thin film may be applied to an organic semiconductor layer for an electronic device, or a carrier transport layer, e.g., a channel layer. The electronic device including the same may have improved electrical properties, e.g., relatively high charge mobility, as well as improved processibility and workability.

The organic thin film may be manufactured by depositing the fused polycyclic heteroaromatic compound on a substrate according to the general method or dissolving the fused polycyclic heteroaromatic compound in an organic solvent and then coating the same at room temperature according to a solution process. If required, heating treatment may be performed after the deposition or coating process to further enhance the densification and uniformity of the thin film.

Particularly, the organic solvent may include at least one kind of general organic solvent, for example, at least one kind of an aliphatic hydrocarbon solvent (e.g., hexane, heptane, etc.); an aromatic hydrocarbon solvent (e.g., toluene, pyridine, quinoline, anisole, mesitylene, xylene, etc.); a ketone-based solvent (e.g., methyl isobutyl ketone, 1-methyl-2-pyrrolidinone, cyclohexanone, acetone, etc.); an ether-based solvent (e.g., tetrahydrofuran, isopropyl ether, etc.); an acetate-based solvent (e.g., ethyl acetate, butyl acetate, propylene glycol methyl ether acetate, etc.); an alcohol-based solvent (e.g., isopropyl alcohol, butanol, etc.); an amide-based solvent (e.g., dimethyl acetamide, dimethyl formamide, etc.); a silicone-based solvent; and a mixture of solvents. The amount of the fused polycyclic heteroaromatic compound dissolved in the organic solvent may be adequately selected and determined by a person of ordinary skill in the art, for example, in a range of about 0.01 wt % to about 50 wt % in the total solvent in the view of solubility and coating property.

The method of providing an organic thin film may include thermal deposition, vacuum deposition, laser deposition, screen printing, printing, imprinting, spin casting, dipping, inkjetting, roll coating, flow coating, drop casting, spray coating, roll printing, etc., but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, and is specifically in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, a sensor, etc., and the organic thin film may be applied to each device according to the general process commonly known in the art.

For example, the transistor includes a gate electrode disposed on a substrate; a source electrode and a drain electrode facing each other and defining a channel region; an insulation layer electrically insulating the source electrode and drain electrode and the gate electrode; and an active layer including the fused polycyclic heteroaromatic compound formed in the channel region.

The active layer may be obtained by depositing the fused polycyclic heteroaromatic compound, or applying a composition including the fused polycyclic heteroaromatic compound to a solution process, e.g., screen printing, printing, spin coating, dipping, ink jetting, etc. When the active layer is formed by the solution process, the process cost may be reduced, and a wide area device may be effectively manufactured.

Figure 2:
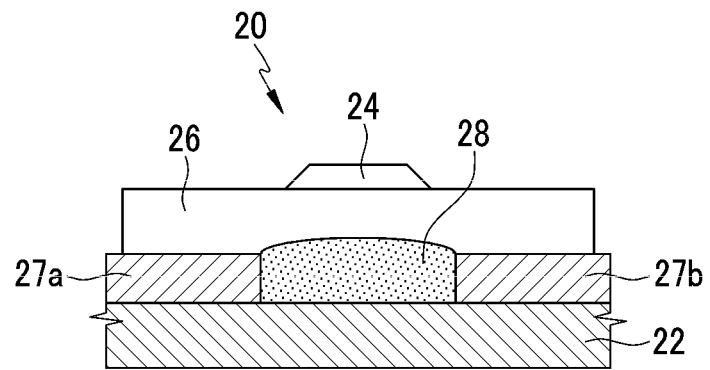
FIG. 2 is a schematic cross-sectional view showing a transistor according to example embodiments.

FIGS. 1 and 2 are schematic cross-sectional views showing a transistor according to example embodiments. The transistor according to example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. On the insulation layer 16, a source electrode 17a and a drain electrode 17b defining a channel region are provided, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed on the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic (e.g., polyethylene naphthalate (PEN), polyethylene terephthalate (PET), polycarbonate, polyvinyl alcohol, polyacrylate, polyimide, polynorbornene, and polyethersulfone (PES)), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but is not limited thereto.

The insulation layers 16 and 26 may include: a generally-used insulator having a relatively high dielectric constant, particularly a ferroelectric insulator (e.g., $Ba_{0.33}Sr_{0.66}TiO_3$ (BST, barium strontium titanate), $Al_2O_3$, $Ta_2O_5$, $La_2O_5$, $Y_2O_3$, and $TiO_2$); an inorganic insulator (e.g., $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$ (x is determined depending on valence of Si), AlON (aluminum oxy nitride), etc.); or an organic insulator (e.g., polyimide, benzocyclobutane (BCB), parylene, polyacrylate, polyvinyl alcohol, polyvinylphenol, etc.), but is not limited thereto.

Hereinafter, the example embodiments are illustrated in more detail with reference to examples. However, these are examples, and the present disclosure is not limited thereto.

EXAMPLE

Example 1: Synthesis of Fused Polycyclic Heteroaromatic Compound

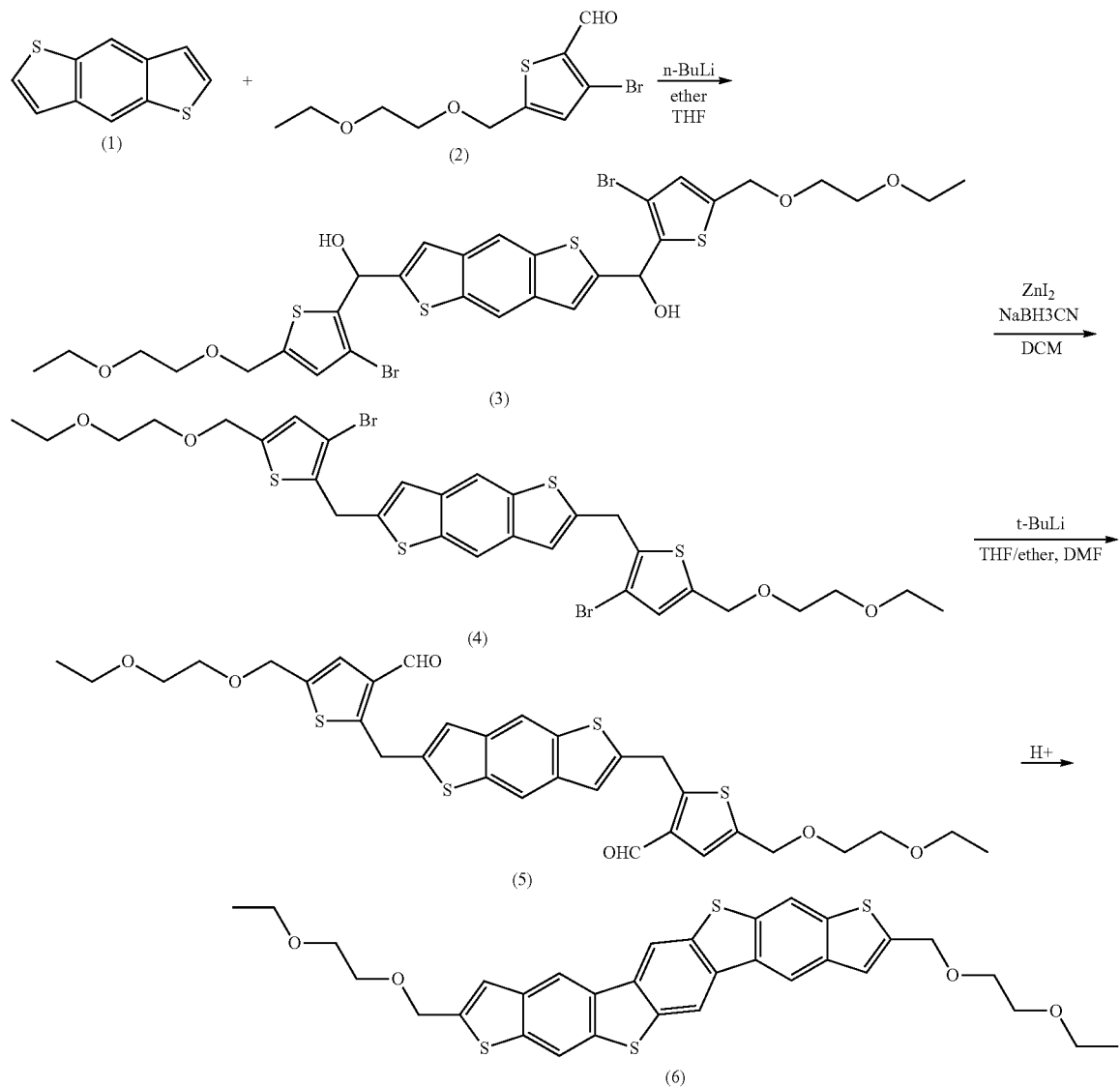

A diol compound (3) is synthesized by adding 3.74 g (19.68 mmol) of n-butyl lithium to benzodithiophene (a compound (1)) at −78° C. under an ether and tetrahydrofuran (THF) solvent and then, 15 g (51.61 mmol) of a hetero aromatic ring compound substituted with bromine (a compound (2)) thereto in Reaction Scheme 1.

Then, 10.6 g (13.65 mmol) of the diol compound (the compound (3)) is dissolved in a dichloromethane solvent, NaBH$_3$CN (87.35 mmol) and ZnI$_2$ are added thereto, and the mixture is deoxygenated at 0° C., obtaining a compound (4).

After adding t-butyl lithium to an ether and tetrahydrofuran solvent at −78° C., a solution obtained by dissolving the compound (4) in dimethyl formamide (DMF) is added thereto, obtaining an aldehyde compound (5). The aldehyde compound (5) is dehydrocyclized under an acid catalyst, e.g., Amberlyst for 24 hours and then, filtered, obtaining a compound (6).

MALDI-TOF MS measurement value: 606.087

Example 2: Manufacture of Organic Thin Film Transistor (OTFT)

First of all, chromium is deposited through sputtering to form a 1000 Å-thick gate electrode on a clean glass substrate, and SiO$_2$ is deposited to form a 3000 Å-thick insulation layer in a CVD method. Then, Au is deposited thereon to be 700 Å-thick through sputtering to form a source electrode and a drain electrode. The glass substrate is used with isopropyl alcohol for 10 minutes before coating an organic semiconductor material. In addition, the SiO$_2$ used as the insulation layer is treated with UV/O$_3$ for 30 minutes before modifying the surface.-

Then, a product obtained above is dipped in an octyl-trichlorosilane solution diluted to have a concentration of 10 mM for 30 minutes, cleaning the product with polyvalent hexane and alcohol, and drying the product and then, thermally depositing the compound according to Example 1 at a speed of 0.2 Å/sec under relatively high vacuum (5×10$^{-6}$ torr) to form a 1,000 Å-thick active layer 18, manufacturing an organic thin film transistor (OTFT) device 10 having a structure shown in FIG. 1.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A fused polycyclic heteroaromatic compound represented by Chemical Formula 1B:

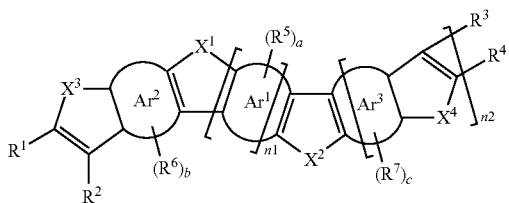

Chemical Formula 1B wherein, in Chemical Formula 1B,
each of $Ar^1$, $Ar^2$, and $Ar^3$ are independently selected from phenylene, naphthalene, and anthracene,
a, b and c correspond to a number of hydrogens bound to a carbon of $Ar^1$, $Ar^2$, and $Ar^3$,
each of $X^1$ and $X^2$ are independently selected from S, Se, Te, and N—$R^a$, wherein $R^a$ is independently selected from hydrogen and a linear or branched $C_1$ to $C_{10}$ alkyl group,
each of $X^3$ and $X^4$ are independently selected from O, S, Se, Te, N—$R^a$, and $C(R^b)$=$C(R^c)$, wherein $R^a$, $R^b$, and $R^c$ are independently selected from hydrogen and a linear or branched $C_1$ to $C_{10}$ alkyl group,
each of $R^1$ to $R^7$ are independently selected from hydrogen, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group,
one of $R^1$ and $R^2$, and $R^3$ and $R^4$, are linked with each other to provide one of a $C_5$ aromatic ring and a $C_6$ aromatic ring,
n1 is 1 or 2,
n2 is 0 or 1,
n1+n2 is greater than or equal to 1, and
at least one hydrogen of the aromatic ring at an outermost position of Chemical Formula 1B is substituted with a functional group represented by Chemical Formula 2,

[Chemical Formula 2]

wherein, in Chemical Formula 2,
L is selected from a single bond, a substituted or unsubstituted $C_1$ to $C_{20}$ alkylene group, a substituted or unsubstituted $C_3$ to $C_{30}$ arylene group, and a substituted or unsubstituted $C_3$ to $C_{30}$ heteroarylene group,
each of $Y^1$ and $Y^2$ are independently selected from O, S, Se, Te, and NH,
each of $R^p$ and $R^q$ are independently selected from hydrogen and a $C_1$ to $C_6$ alkyl group,
each of $R^r$, $R^s$, $R^x$, $R^y$, and $R^z$ are independently selected from hydrogen, a $C_1$ to $C_6$ alkyl group, a $C_6$ to $C_{10}$ aryl group, and a $C_3$ to $C_{10}$ heteroaryl group,
p is an integer ranging from 1 to 5,
q is an integer ranging from 1 to 30, and
r is an integer ranging from 0 to 2.

2. The fused polycyclic heteroaromatic compound of claim 1, wherein in Chemical Formula 1B, each of $X^1$, $X^2$, $X^3$, and $X^4$ are independently one of a sulfur atom (S) and a selenium atom (Se).

3. The fused polycyclic heteroaromatic compound of claim 1, wherein in Chemical Formula 1B, $X^1$ and $X^2$ are sulfur atoms (S), and $X^3$ and $X^4$ are selenium atoms (Se).

4. The fused polycyclic heteroaromatic compound of claim 1, wherein the one of the $C_5$ aromatic ring and $C_6$ aromatic ring are independently an $X^5$-containing ring and an $X^6$-containing ring, the $X^5$ and $X^6$ are independently selected from O, S, Se, Te, N—$R^a$, and $C(R^b)$=$C(R^c)$, wherein $R^a$, $R^b$, and $R^c$ are independently selected from hydrogen and a linear or branched $C_1$ to $C_{10}$ alkyl group.

5. The fused polycyclic heteroaromatic compound of claim 1, wherein
at least one of $R^1$ and $R^4$ of Chemical 1B is a polar functional group of Chemical Formula 2; and
the fused polycyclic heteroaromatic compound of Chemical Formula 1B is linear.

6. The fused polycyclic heteroaromatic compound of claim 1, wherein the L of Chemical Formula 2 is represented by Chemical Formula 3:

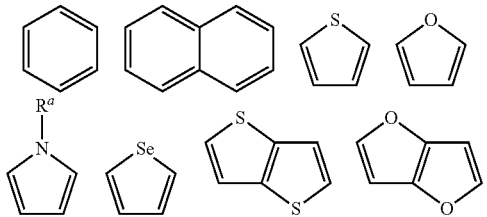

-continued

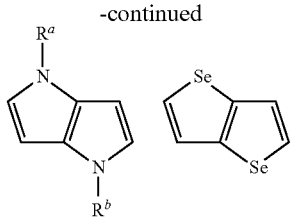

wherein, in Chemical Formula 3,
each of $R^a$ and $R^b$ are independently selected from hydrogen and a linear or branched $C_1$ to $C_{10}$ alkyl group.

7. The fused polycyclic heteroaromatic compound of claim 1, wherein the fused polycyclic heteroaromatic compound has an average molecular weight of about 300 to about 3,000.

8. The fused polycyclic heteroaromatic compound of claim 1, wherein the fused polycyclic heteroaromatic compound is at least one of compounds (16), (18), (20), (22) and (24):

(16)
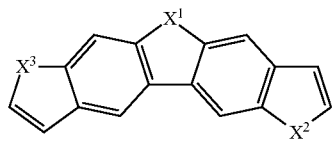

(18)
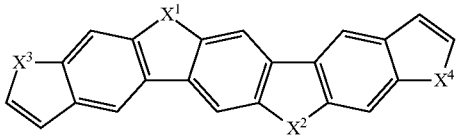

(20)
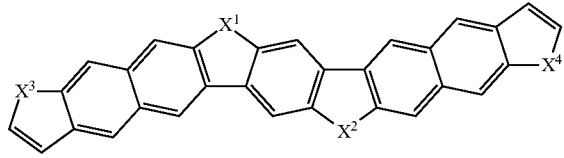

(22)
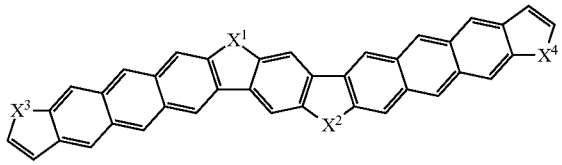

(24)
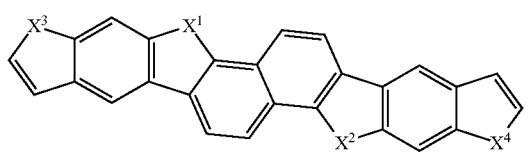

wherein, in the compounds (16), (18), (20), (22) and (24),
each of $X^1$, $X^2$, $X^3$, and $X^4$ are the same in Chemical Formula 1B,
a hydrogen of each aromatic ring is optionally replaced by a $C_1$ to $C_{10}$ linear or branched alkyl group, and
at least one hydrogen in an outermost aromatic ring is optionally replaced by the substituent represented by Chemical Formula 2.

9. An organic thin film comprising the fused polycyclic heteroaromatic compound of claim 1.

10. An electronic device comprising the fused polycyclic heteroaromatic compound of claim 1.

11. The electronic device of claim 10, wherein the electronic device is one of a transistor, an organic light emitting diode (OLED), a photovoltaic device, a solar cell, a laser device, a memory device, and a sensor.

* * * * *